United States Patent [19]
Ozaki et al.

[11] Patent Number: 5,202,444
[45] Date of Patent: Apr. 13, 1993

[54] OPTICALLY ISOMERIC INOSITOL AND PROCESS FOR MAKING OPTICALLY ACTIVE COMPOUND

[75] Inventors: Shoichiro Ozaki; Takahiko Akiyama, both of Matsuyama; Kunio Kageyama, Yokohama; Morihisa Machida, Kanagawa, all of Japan

[73] Assignee: The Yokohama Rubber Co., Ltd., Tokyo, Japan

[21] Appl. No.: 795,801

[22] Filed: Nov. 21, 1991

[30] Foreign Application Priority Data

Nov. 27, 1990 [JP] Japan ................... 2-323779

[51] Int. Cl.$^5$ ........................... C07D 317/72
[52] U.S. Cl. ................... 549/214; 549/341; 549/342
[58] Field of Search ............... 549/214, 432, 448, 341, 549/342

[56] References Cited

PUBLICATIONS

S. D. Gero, CA 64 (1966) 14249h.
K. H. Scheit et al, CA 65-17035h (1966).
S. J. Angyal et al, CA 55-11316g (1961).
S. J. Angyal et al. CA 56-6068g-6071a (1962).
Brown et al, JACS 1984, 106, 1531-1533.
Evans et al, JACS 1985, 107, 4346-4348.
Diastereoselective Reduction of α-Keto Esters Bearing Chiro-Inositol Derivatives as Chiral Auxiliaries, Takahiko Akiyama et al, Tetrahedron Letters, vol. 32, No. 10, pp. 1335-1338 (1991).
Diastereoselective Reduction of –Keto Amides Having, etc., Yasuhiro Kawanami et al, Chem. Lett., pp. 2021-2024 (1987).
Diastereoselective Reduction of a –Keto Amides Having, etc. Yasuhiro Kawanami et al., Bull Chem Soc., Japn. 62, p. 3598 (1989).
J. Am. Chem. Soc., 107 p. 4346 (1985).
J. Am. Chem. Soc., 106 p. 1531 (1984).
Chem. Lett. p. 1897 (1986).

*Primary Examiner*—Cecilia Tsang
*Attorney, Agent, or Firm*—Finnegan, Henderson, Farabow, Garrett & Dunner

[57] ABSTRACT

Optically active diols and hydroxycarboxylic acids and their esters are produced by deriving 1L-1,2:5,6-di-O-cyclohexylidene-chiro-inositol from 1L-chiro-inositol as an asymmetric source, followed by introduction of a selected class of sterically hindering and asymmetrically reactive groups into the first-mentioned compound and by subsequent reduction of the resulting compound. Seven specific inositols are also derivable from synthesis of those ultimate compounds.

7 Claims, 8 Drawing Sheets

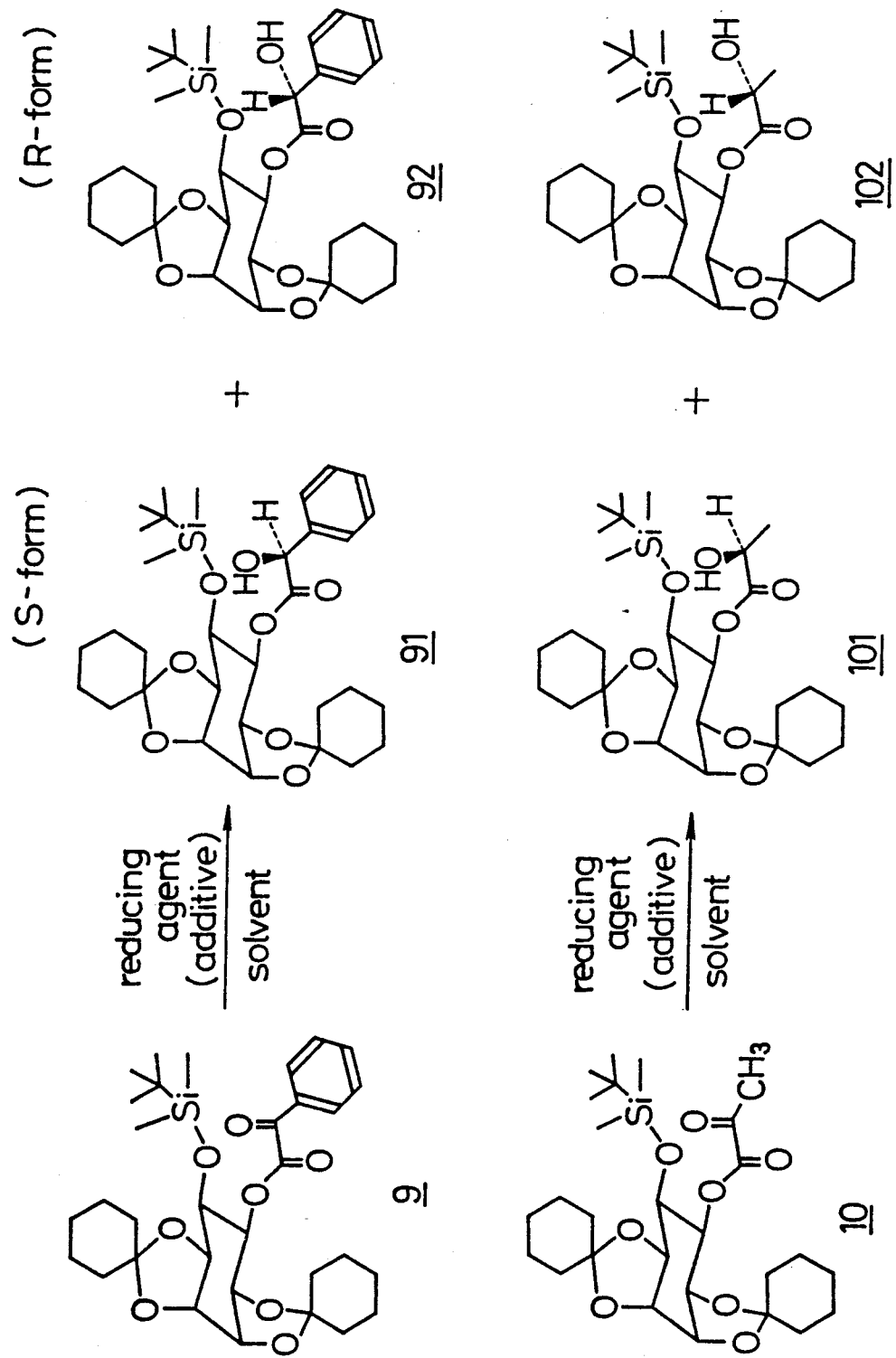

OPTICALLY ISOMERIC INOSITOL AND PROCESS FOR MAKING OPTICALLY ACTIVE COMPOUND

BACKGROUND OF THE INVENTION

1. Technical Field

This invention relates to optically isomeric inositol compounds and further to a process for preparing diols, or hydroxycarboxylic acids or their esters, all of optical activity, which have utility as intermediates or modifiers for the production of medicines or antibiotics. Such inositols result as intermediate products from synthesis of the optically active ultimate compounds.

2. Prior Art

Pairs of optical isomers exist which differ little in structure. Yet, despite their close similarity, one isomer of such a pair may be of great practical significance for example for medicinal use, and the other isomer may be ineffective. To selectively synthesize either desirable isomer of an isomeric pair, continued research has been made with a variety of asymmetric reactions. Now practically successful are several modes of asymmetric synthesis capable of high selectivity, say 95% or greater.

Certain asymmetric syntheses have heretofore been used for example for preparing hydroxycarboxylic acids or their esters. Details of these syntheses are described below.

In a publication entitled "Asymmetric Syntheses", Y. Inoue and H. Harada, Tokyo Kagaku-Dojin Co. (1973), there is reported an asymmetric reduction reaction for use in the synthesis of α-keto-esters. This known method is susceptible to reduced selectivity and hence decreased productivity.

A highly selective reaction of reduction is employed to derive optically active α-keto-amides as disclosed in and Bull. Chem. Soc., Japan, 62, p. 3598 (1989). In that instance, adverse racemization will often take place upon hydrolysis of the amide into an α-hydroxycarboxylic acid.

An oxidation reaction is taught for the synthesis of α-hydroxycarboxylic acids in J. Am. Chem. Soc., 107, p. 4346 (1985). As reported in J. Am. Chem. Soc., 106, p. 1531 (1984), α-keto-esters are produced through a reduction reaction in which an asymmetric coordinator is utilized.

The foregoing asymmetric syntheses of the prior art have the drawback that they tend to cause side reactions and objectionable racemization, thus involving low production yield and tedious optical resolution. This latter step of resolution is responsible for poorer productivity.

SUMMARY OF THE INVENTION

It is therefore one object of the present invention to provide novel, optically isomeric compounds of an inositol family.

Another object of the invention is to provide a process for preparing diols, or hydroxycarboxylic acids or their esters, all such compounds having optical activity. This process contemplates the use of a unique mode of asymmetric reaction incorporating a specific inositol derivative as an asymmetric source. Thus, the ultimate compound is obtainable as a diastereomer at high levels of selectivity and of productivity and without need of optical resolution. The process of the invention is also feasible in preparing those compounds which are inherently optically active but have been difficult to optically resolve.

Many other objects and advantages of the invention will be better understood from the following description with reference to the accompanying drawings.

BRIEF DESCRIPTION OF THE DRAWINGS

FIGS. 1A to 1C, FIGS. 2A to 2C, FIG. 3 and FIG. 4 are schematic views showing the sequences of reaction of the process according to the present invention and the routes from a starting asymmetric source to the respective desired compounds.

DETAILED DESCRIPTION OF THE INVENTION

According to one aspect of the present invention, the following inositol compounds of a specific configuration are provided as labeled for convenience as A to G.

Figure 1A:
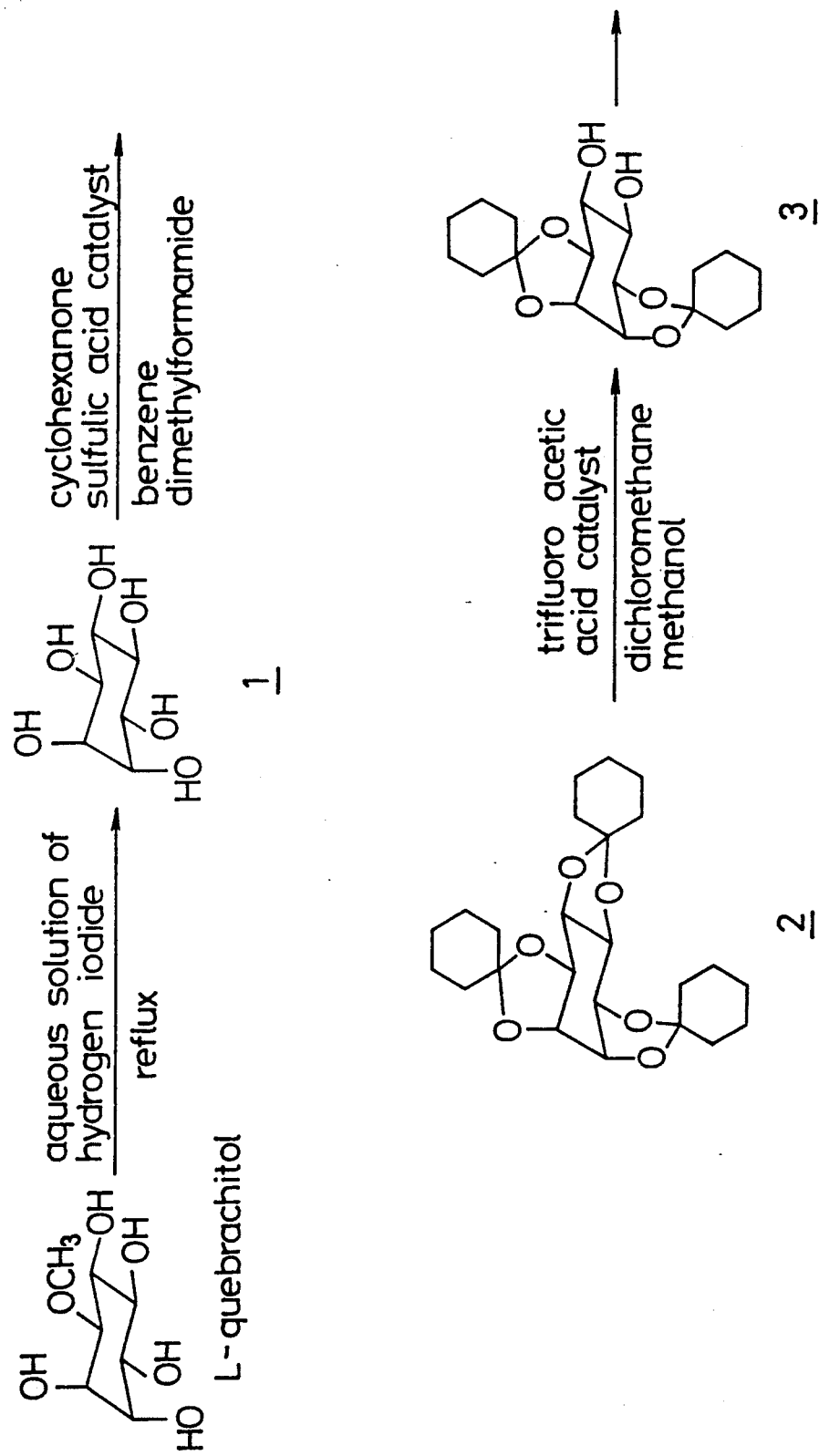
Figure 1B:
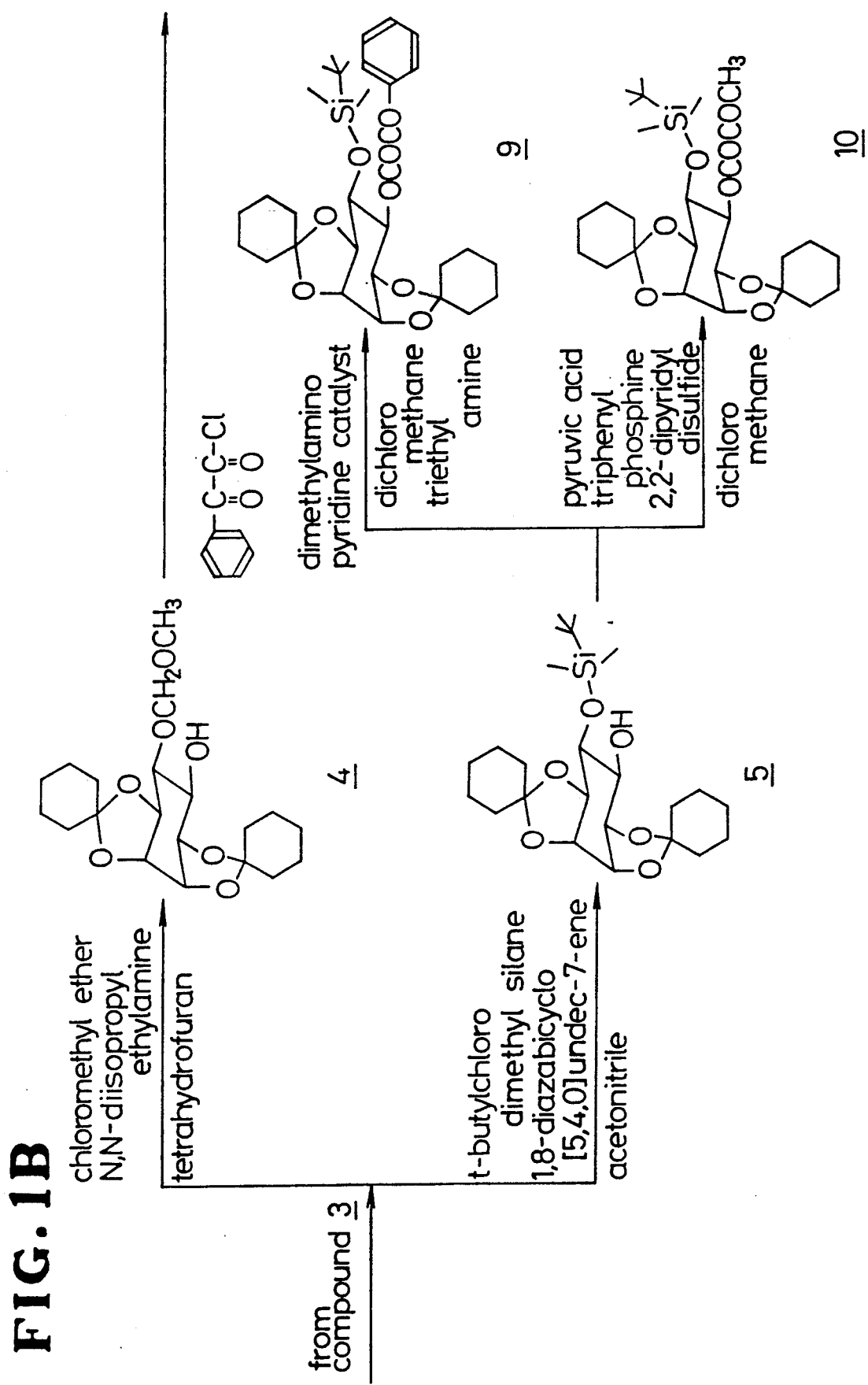
Figure 1C:
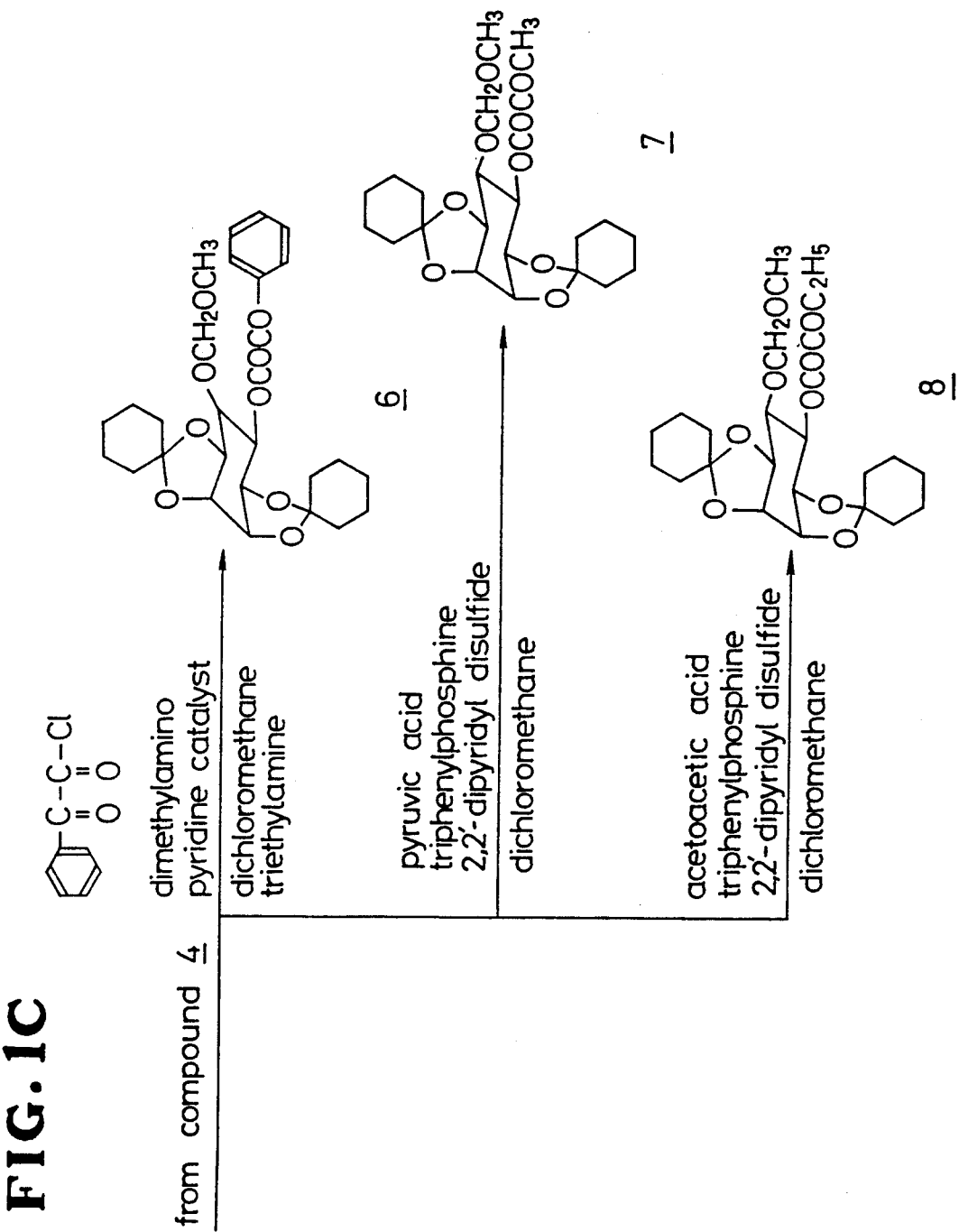

A: 1L-1,2:5,6-di-O-cyclohexylidene-3-O-methoxymethylchiro-inositol
B: 1L-3-O-t-butyldimethylsilyl-1,2:5,6-di-O-cyclohexylidene-chiro-inositol
C: 1L-3-O-benzoylcarbonyl-1,2:5,6-di-O-cyclohexylidene-4-O-methoxymethyl-chiro-inositol
D: 1L-3-O-acetylcarbonyl-1,2:5,6-di-O-cyclohexylidene-4-O-methoxymethyl-chiro-inositol
E: 1L-3-O-propionylcarbonyl-1,2:5,6-di-O-cyclohexylidene-4-O-methoxymethyl-chiro-inositol
F: 1L-4-O-benzoylcarbonyl-3-O-t-butyldimethylsilyl-1,2:5,6-di-O-cyclohexylidene-chiro-inositol
G: 1L-4-O-acetylcarbonyl-3-O-t-butyldimethylsilyl-1,2:5,6-di-O-cyclohexylidene-chiro-inositol The above compounds are isolated as intermediates during synthesis of specific optically active diols and hydroxycarboxylic acids and their esters described later. More specifically, these compounds are shown in FIGS. 1A to 1C, namely compound A at 4, compound B at 5, compound C at 6, compound D at 7, compound E at 8, compound F at 9 and compound G at 10. Compounds A to G are by nature oily among which compounds C, D, F and G are rather yellowish.

Another aspect of the invention provides a process for preparing diols, or hydroxycarboxylic acids or their esters, all of optical activity, which process comprises the steps of (a) deriving a second compound or 1L-1,2:5,6-di-O-cyclohexylidene-chiro-inositol from a first compound or 1L-chiro-inositol as an asymmetric source, (b) introducing into the second compound a sterically hindering group at either one of the 3 and 4 positions and an asymmetrically reactive group at the other position, and (c) reducing the resulting compound. A modified form of the process according to the invention further comprises hydrolysis at the reduction step.

Referring now to the drawings, FIGS. 1A to 1C illustrate the reaction steps from demethylation of L-quebrachitol to introduction of two different functional groups via preparation of 1L-chiro-inositol thereby obtaining 1L-1,2:5,6-di-O-cyclohexylidene-chiro-inositol. FIGS. 2A to 2C and FIGS. 3 and 4 shows various subsequent reaction steps.

To implement the process of the invention, 1L-chiroinositol is used as an asymmetric source, the compound being designated at 1 in FIG. 1A. Compound 1 may be derived, though not restricted, preferably from demethylation of L-quebrachitol at a methoxy group bonded to the 2 position. The reaction of demethylation is not specifically limitive but conveniently relies on the method of S. J. Angyal and R. M. Hoskins, "Methods in Carbohydr. Chem.", 2, p. 87 (1963).

L-Quebrachitol as a starting material for compound 1 is an inositol monomethyl ether that is L-(−)-2-O-methyl-chiro-inositol. It finds a source of supply from quebraco barks, Hevea brasiliensis or para rubber trees and many other plants. This compound may be made easily available from serums as disclosed for instance in Japanese Patent Laid-Open Publications 2-19332 (1990) and 1-161922 (1989). The serum is byproduced upon coagulation and removal of rubber components from a natural rubber latex. The byproduct is treated concentrate or solid and dissolved in methanol, followed by concentration of the solution, after which L-quebrachitol is collected in crystalline form. The resultant compound is optically active and levorotary in nature.

Compound 1 is masked at its six hydroxyl groups and at each adjacent pair with use of a bridge type protecting group such as cyclohexanone, acetone or the like, cyclohexanone being shown in FIG. 1A. Masking may be done in the presence of an acidic material such as sulfuric acid or with the addition of an enol ether of the protecting material, i.e. 1-ethoxycyclohexene in the case of cyclohexanone or 2,2-dimethoxypropane in the case of acetone.

Protection of compound 1 leads to 1L-1,2:3,4:5,6-tri-O-cyclohexylidene-chiro-inositol 2. On subsequent unmasking at the 3 and 4 positions by treatment with trifluoro acetate, compound 2 turns into 1L-1,2:5,6-di-O-cyclohexylidene-chiro-inositol 3.

Compound 3 is of an optically active configuration with a $C_2$-axis of symmetry. This compound has at the 3 and 4 positions two hydroxyl groups to which functional groups may be optionally attached. In the practice of the invention, a sterically hindering group is introduced into one of the hydroxyl groups and an asymmetrically reactive group into the other. Suitable functional groups for use in steric hindrance include alkoxyalkyl ethers such as methoxymethyl ether, ethoxyethyl ether, methoxyethyl ether and the like, and alkylsilyl ethers and arylsilyl ethers such as t-butyldimethylsilyl ether, t-butyldiethylsilyl ether, phenyldimethylsilyl ether, phenyldiethylsilyl ether and the like. Functional groups useful for asymmetric reaction are those capable of forming keto-esters.

To incorporate a sterically hindering group selected, compound 3 may be reacted with a chloromethyl group-, chloroethyl group- or chlorobenzyl group-containing compound or a silyl chloride compound. The chloromethyl group-containing compound is chosen from chloromethylmethyl ether, chloromethylethyl ether, chloromethyloctyl ethyl, chloromethyl anisole, 4-chloromethyl biphenyl, 1-(chloromethyl)-2,5-dimethoxy benzene, 4-chloromethyl-α-phenyl anisole, 1-chloromethyl naphthalene, 1-cholormethyl-2-methyl naphthalene, 9-chloromethyl anthracene, chloromethylphenyl sulfide, chloromethylphenyl sulfone, chloromethyldiisopropoxy silane, chloromethyldiisopropoxymethyl silane, chloromethyldimethylphenyl silane, chloromethyltrimethyl silane and the like. The chloroethyl group-containing compound includes 2-chloroethylmethyl ether, 2-chloroethylethyl ether, 2-chloroethyl benzene, 2-chloroethylmethyl sulfide, 2-chloroethylethyl sulfide, 2-(2-chloroethyl)-α,α,α-trifluoro toluene and the like. The chlorobenzyl-containing compound is 4-t-butylbenzyl chloride and the like. Specific examples of the silyl chloride compound are t-butyldimethylsilyl chloride, t-butyldiphenylsilyl chloride, dimethylhexylsilyl chloride, dimethylethylsilyl chloride, dimethylisopropylsilyl chloride, dimethyloctadecylsilyl chloride, dimethyloctylsilyl chloride, dimethylphenylsilyl chloride, diphenylmethylsilyl chloride, tributylsilyl chloride, tribenzylsilyl chloride, trihexylsilyl chloride, triisobutylsilyl chloride, triisopropylsilyl chloride and the like.

As keto-ester forming compounds introduced for asymmetric reaction, there is used one group of acid chlorides of the formula

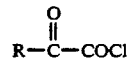

where R is a saturated or aromatic hydrocarbon group. Specific examples include pyruvic acid chloride, benzoyl fumarate chloride (phenylglyoxyloyl chloride) and the like. The acid chlorides of this group are suitable in preparing α-keto-carboxylic acids. Where β- or higher-keto-carboxylic acids are preferred, another group of acid chlorides is selected which is represented by the formula

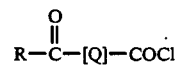

where R is a saturated or aromatic hydrocarbon group, and Q is —$CH_2$—, —$CHC_2H_5$—, —$C(C_2H_5)_2$—, —$(CH_2)_n$, n being from 2 to 8, or

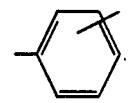

Alternatively, keto-esters may be rendered available by the use of α-, β-, γ-, δ- or higher-carboxylic acids in place of the acid chlorides and with the help of esterification. After etherification is effected to sterically hinder either one hydroxyl group of compound 3, a given acid chloride or carboxylic acid is reacted with the remaining hydroxyl group.

As depicted in FIG. 1B, compound 3 is reacted with chloromethylmethyl ether or t-butylchlorodimethyl silane to thereby give 1L-1,2:5,6-di-O-cyclohexylidene-3-O-methoxymethyl-chiro-inositol 4 (compound A) or 1L-3-O-t-butyldimethylsilyl-1,2:5,6-di-O-cyclohexylidene-chiroinositol 5 (compound B). Compounds 4 and 5 each have an auxiliary chiral group. Although N,N-diisopropylethyl amine is added for the synthesis of compound 4 and 1,8-diazabicyclo[5.4.0]undec-7-ene (DBU) for the synthesis of compound 5, these additives are not entrained in compounds 4 and 5. Both additives merely act as a cosolvent or a catalyst.

Subsequent reactions of each of compounds 4 and 5 with acid chlorides give 1L-3-O-benzoylcarbonyl-1,2:5,6-di-O-cyclohexylidene-4-O-methoxymethyl-chiro-inositol 6 (compound C), 1L-3-O-a-cetylcarbonyl-1,2:5,6-di-O-cyclohexylidene-4-O-methoxymethyl-chiro-inositol 7 (compound D), 4-O-methoxymethyl-chiro-inositol 8 (compound E), 1L-4-O-benzoylcarbonyl -3-O-5-butyldimethylsilyl-1,2:5,6-di-O-cyclohexylidene-chiro-inositol 9 (compound F) and 1L-4-O-acetylcarbonyl-3-O-t-butyldimethylsilyl-1,2:5,6-di-O-cyclohexylidene-chiro-inositol 10 (compound G), all of α-keto-esters. These reaction routes are shown in FIGS. 1B and 1C.

Upon completion of the introduction of both sterically hindering and asymmetrically reactive groups, reduction and if necessary hydrolysis are carried out so that diastereomer mixtures are formed with varying selectivity ratios. A selected class of reducing agents or other additives is incorporated to initiate or otherwise facilitate the reduction reaction.

Figure 2A:
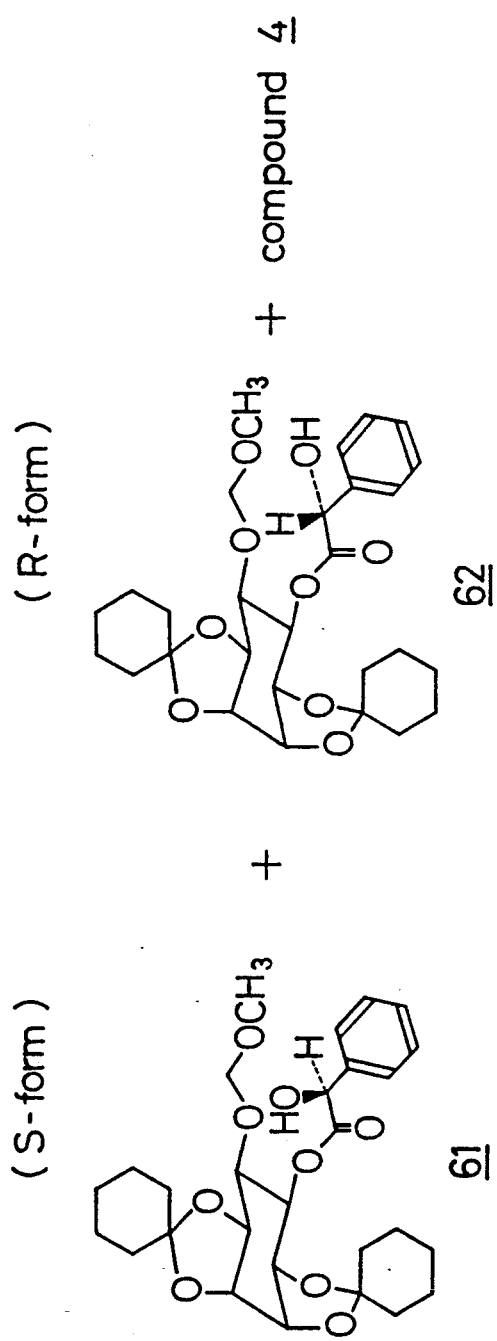
Figure 2B:
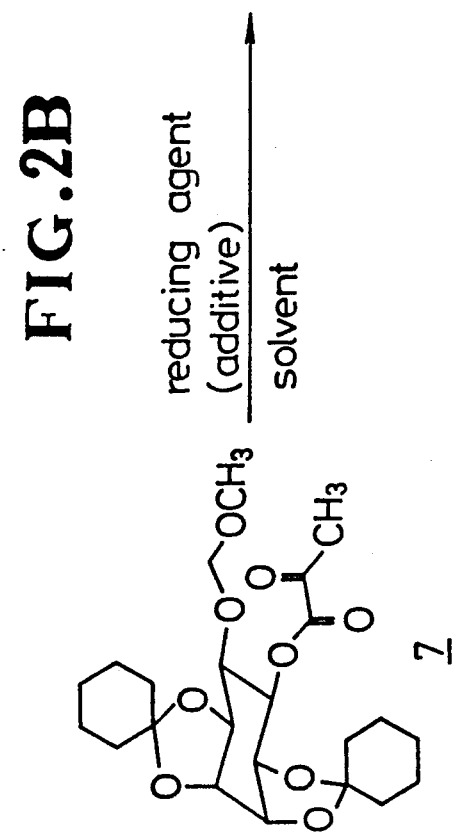
Figure 2B:
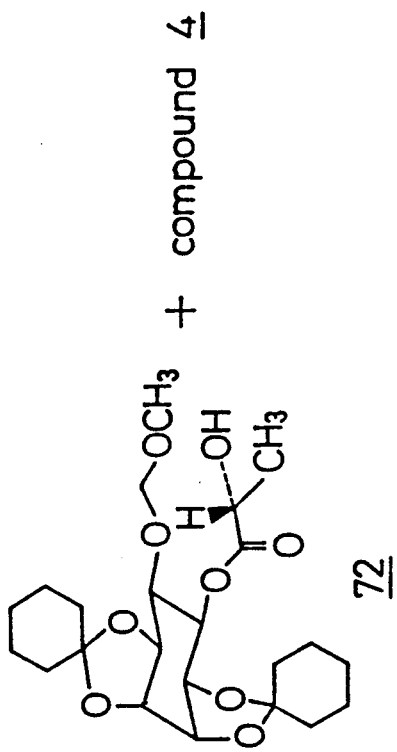
Figure 2B:
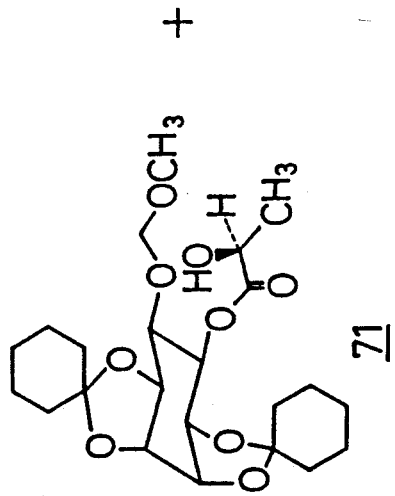
Figure 2C:
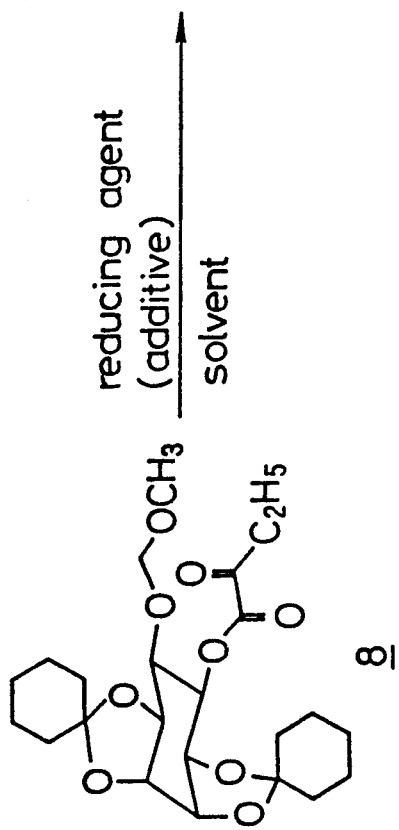
Figure 2C:
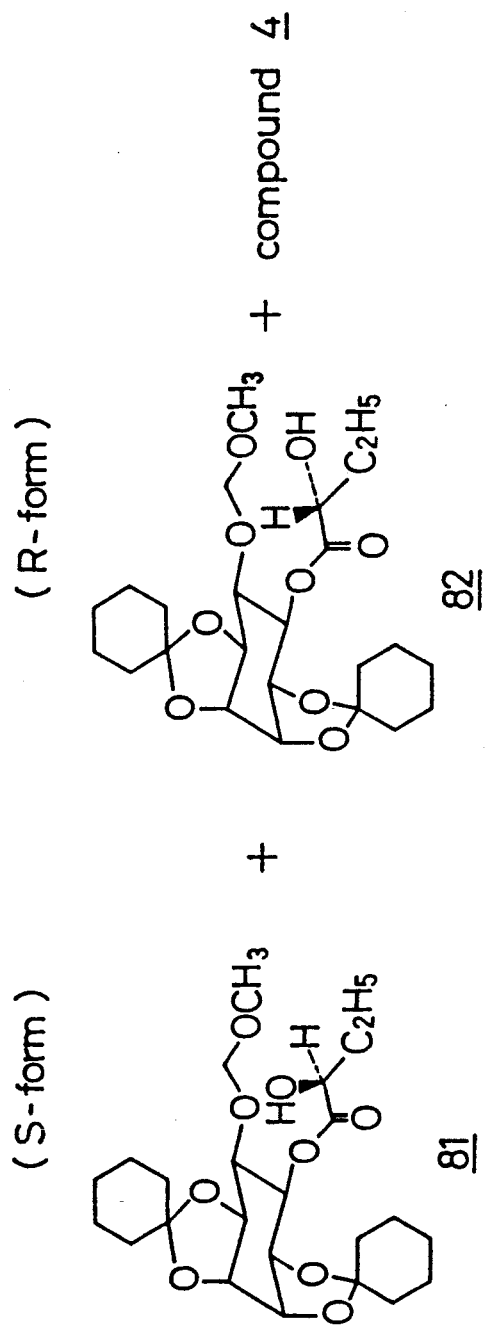

Compounds 6 to 8 are represented in FIGS. 2A to 2C as regards the routes of reduction. Table 1 lists the ratios of diastereomers depending upon the kind of reducers and upon the kind of and the presence or absence of additives. Determination is made by integration of the spectra based on $^1$H-NMR at 270 MHz.

To specify a particular configuration of an optical isomer, the prefixes R and S are used here and below. This is a procedure proposed by R. S. Cahn, C. Ingold and V. Prelog in 1956. A sequence of priority is assigned to the four atoms or groups of atoms attached to the chiral center. If the groups are seen to proceed from the highest priority to the second and then to the third in a clockwise direction, the configuration is specified R. If counterclockwise, the configuration is specified S.

When compound 6 is reacted in diethyl ether and in the presence of $KB[CH(CH_3)C_2H_5]_3H$ (K-Selectride, tradename, reducing agent), a diastereomer is obtained predominantly of an S configuration with a high selectivity ratio of S to R of 97 to 3 as shown in Table 1. Through recrystallization of the diastereomer, 1L-1,2:5,6-di-O-cyclohexylidene-3-O-[(2S)-2-hydroxy-2-phenylacetyl]-4-O-methoxymethyl-chiro-inositol 61 is isolated as a diastereomer of an S form in a yield of greater than 99.9%.

Compound 6 may be reduced with addition of a given additive to thereby attain reversed selection. An R form is thus predominant as is clear also from Table 1.

Figure 3:
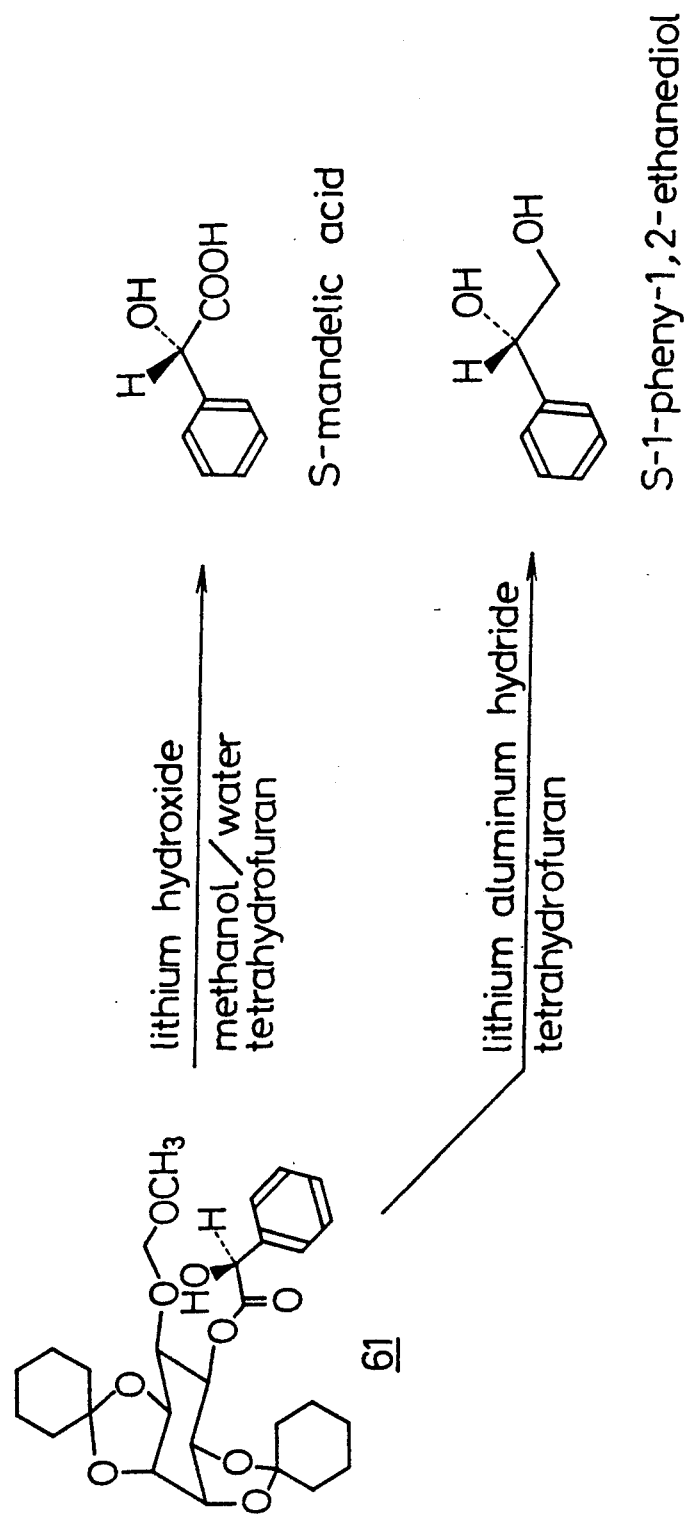

Hydrolysis and subsequent reduction of compound 61 are depicted in FIG. 3. This hydrolysis gives optically active S-mandelic acid without involving racemization. By reduction of the resultant compound, there is produced S-1-phenyl-1,2-ethane diol of optical activity.

Compounds 9 and 10 are shown reduced in FIG. 4 in which compound 9 is 1L-4-O-benzoylcarbonyl-3-O-t-butyldimethylsilyl-1,2:5,6-di-O-cyclohexylidene-chiroinositol, and compound 10 is 1L-4-O-acetylcarbonyl-3-O-t-butyldimethylsilyl-1,2:5,6-di-O-cyclohexylidene-chiroinositol. Both compounds have bonded a t-butyldimethylsilyl group of a bulky or multichained structure. In Table 2 the ratios of diastereomers are tabulated which have been obtained with reducers varied and with additives varied or omitted. The diastereomers are easily separable into their R and S forms by silica gel column chromatography.

Selectivity between R and S forms is variable, as is apparent from Table 2, not only with the kind of reducers but also with the nature of additives and solvents. To be more specific, an S form is highly selectively derivable with an S to R ratio of 96 to 4 when compound 9 is subject to a reduction reaction with use of diethyl ether or tetrahydrofuran as a solvent and K-Selectride as a reducing agent. In the case of combination of 18-crown-6 as an additive, however, an R form predominates with an R to S ratio of 96 to 4.

A reducing agent, $LiB[CH(CH_3)C_2H_5]_3H$ (L-Selectride, tradename), is highly sensitive to the nature of solvents in terms of configurational selectivity. A combination of that agent with diethyl ether is satisfactory as an S form is producible with an S to R ratio of 96 to 4. To replace the solvent with tetrahydrofuran causes a sharp decline in selectivity. Even with L-Selectride combined with tetrahydrofuran, but if hexamethylphosphoric triamide (HMPA) is incorporated as an additive, an R form can be highly selectively obtained with an R to S ratio of 91 to 9.

Similar reasoning is applied as such to compound 10 where K-Selectride is used in combination with tetrahydrofuran. Compound 10 is interconverted, in that instance, into an S form with a high ratio of 98 as against the corresponding R form. Incorporation of an additive renders selectivity reversible but at too low a level. In deriving an S form in a content of 75% or greater, it is preferred to use a reducing agent of the formula $MB[CH(CH_3)C_2H_5]_3$ where M is lithium or potassium. To selectively derive an R or S form, a reduction reaction is effected with use of an additive selected from HMPA, $[(CH_3)_2N]_3PO$, 18-crown-6, 1,4,7,10,13,16-hexaoxacyclooctadecane, 12-crown-4, 1,4,7,10-tetraoxacyclododecane, N,N,N',N'-tetramethylethylenediamine and $(CH_3)_2NCH_2CH_2N(CH_3)_2$.

Various modifications and variations of the invention are possible in the light of the above disclosure. Any suitable solvent or catalyst or both may be employed, where desired, in each of the reaction steps.

The following examples are given to further illustrate the invention.

Throughout these examples the $^1$H-NMR spectra were determined on a spectrometer at 270 MHz (JEOL GSX-270, tradename, Nippon Electronics Co.) and with tetramethyl silane as an internal reference. Measurement was made of the specific rotational powers by a polarimeter (PM-101, tradename, Union Co.) and the IR spectra by an infrared spectophotometer (EPI-G3, tradename, Hitachi Co.).

EXAMPLE 1

This example shows the routes of reaction from the preparation of an asymmetric source to the introduction of sterically hindering and asymmetrically reactive groups.

(1) Synthesis of 1L-chiro-inositol 1

The aforesaid method of S. J. Angyal and R. N. Hoskins was followed in deriving compound 1 from L-quebrachitol.

(2) Synthesis of 1L-1,2:3,4:5,6-tri-O-cyclohexylidene-chiro-inositol 2

The procedure reported by S. J. Angyal, G. C. Iruinq, D. Rutherford and E. Tate in J. Chem. Soc., p. 6662 (1965) was adopted with some modifications made.

Compound 1 (2.56 g, 14.2 mmol) and cyclohexanone (6.0 ml, 57.9 mmol) were suspended in benzene (40 ml) and dimethyl formamide (10 ml), respectively, followed by addition of concentrated sulfuric acid (0.4 ml). After being put into a Kjeldahl flask equipped with a Dean Stark separator, the whole mixture was refluxed for 6 hours while water having been generated was being removed. The reaction mixture after being cooled at room temperature was poured gradually into a saturated aqueous solution of sodium hydrocarbonate (50 ml). Extraction was done with use of ethyl acetate, after which an organic or ethyl acetate layer was dried over sodium sulfate anhydride and then concentrated to give a crystalline product. By subsequent washing of the product with a small amount of ether, compound 2 was obtained in colorless crystalline form.

compound 2
yield: 4.99 g, 11.9 mmol, 84%
mp: 187°–189° C. (found) 191°–192° C. (reported*) *
S. J. Angyal et al., J. Chem Soc., p. 6662 (1965)
δ($^1$H-NMR)(CDCl$_3$): 1.20–1.96 (30H, m, (CH$_2$)$_{15}$)
3.55–3.68 (2H, m, H-3, 4) 4.26–4.45 (4H, m, H-1, 2, 5, 6)

(3) Synthesis of 1L-1,2:5,6-di-O-cyclohexylidene-chiro-inositol 3

Compound 2 (926 mg, 2.19 mmol) was dissolved in dichloromethane (4 ml) and also in methanol (2 ml) and incorporated at 0° C. with trifluoroacetic acid (2 ml). After being elevated immediately at room temperature, the solution was stirred for 30 minutes and thereafter cooled at 0° C., followed by addition of saturated solutions of sodium sulfate (10 ml), of sodium hydrogencarbonate (20 ml) and of dichloromethane (20 ml) in the order mentioned. Vigorous stirring was done, and a crystalline product having been formed was removed by filtration and the filtrate extracted with dichloromethane. An organic or dichloromethane layer after being dried over sodium sulfate anhydride was concentrated to give a crystalline product. The first- and last-mentioned crystals were put together and washed with a limited amount of ether. There was obtained compound 3 in colorless crystalline form.

compound 3
yield: 723 mg, 2.12 mmol, 97%
mp 207°–209° C. (found) 209°–210° C. (reported as in compound 2)
δ($^1$H-NMR)(CDCl$_3$-CD$_3$OD): 1.30–1.75 (20H, m, (CH$_2$)$_{10}$) 2.50 (2H, brs, OH) 3.43–3.53 (2H, m, H-3, 4) 4.07–4.22 (2H, m, H-2, 5) 4.31–4.38 (2H, m, H-1, 6)

(4-1) Synthesis of 1L-1,2:5,6-di-O-cyclohexylidene-3-O-methoxymethyl-chiro-inositol 4 (compound A)

Compound 3 (449 mg, 1.32 mmol) was dissolved in tetrahydrofuran (12 ml) to which chloromethylmethyl ether (0.50 ml, 6.58 mmol) and N,N-diisopropylethyl amine (0.69 ml, 3.96 mmol). Stirring was conducted at 60° C. for one hour. On cooling of the reaction mixture at room temperature, 1N hydrochloric acid (10 ml) was added to terminate the reaction. Extraction was effected with ethyl acetate, and an ethyl acetate layer was washed with a small amount of a saturated aqueous solution of sodium chloride and then dried over sodium sulfate anhydride and subsequently concentrated. The crude product was purified by silica gel chromatography (hexane/ethyl acetate=3/1). Compound 4 was obtained as an oily product.

compound 4
yield: 463 mg, 1.20 mmol, 91%
δ($^1$H-NMR)(CDCl$_3$): 1.43–1.72 (20H, m, (CH$_2$)$_{10}$) 3.46 (3H, s, OCH$_3$) 3.52–3.62 (2H, m, H-3, 4) 4.17–4.22 (3H, m, OH, H-2, 5) 4.31–4.35 (2H, m, H-1, 6) 4.82, 4.91 (2H, ABq, J=6.4 Hz, CH$_2$)
$[\alpha]^{21}_D = +18.92°$ (c=1.11, CHCl$_3$)
IR (CHCl$_3$): 3500 cm$^{-1}$ (—OH) 2950 cm$^{-1}$ 1440 cm$^{-1}$ 1200 cm$^{-1}$ 1160 cm$^{-1}$ 1100 cm$^{-1}$ 910 cm$^{-1}$ 740 cm$^{-1}$ 650 cm$^{-1}$

(4-2) Synthesis of 1L-3-O-t-butyldimethylsilyl-1,2:5,6-di-O-cyclohexylidene-chiro-inositol 5 (compound B)

Compound 3 (1.24 g, 3.65 mmol) was dissolved in acetonitrile (6 ml). In addition to this solution, 1,8-diazabicyclo[5.4.0]undec-7-ene (1.97 ml, 13.14 mmol) and t-butylchlorodimethyl silane (990 mg, 6.57 mmol) were dissolved, respectively, in acetonitrile (4 ml). Reaction of the three different solutions was made with stirring at room temperature for 3 hours. After termination of the reaction with addition of 1N hydrochloric acid (5 ml), the resultant mixture was extracted with ethyl acetate. Washing of an ethyl acetate layer was done in turn with saturated aqueous solutions of sodium chloride, of sodium hydrogencarbonate and of sodium chloride. The layer thus washed was dried over sodium sulfate anhydride and concentrated in vacuo. The concentrate was silica gel-chromatographed (hexane/ethyl acetate=15/1) to give compound 5.

compound 5
yield: 1.34 g, 2.94 mmol, 80%
δ($^1$H-NMR)(CDCl$_3$): 0.15 (3H, s, CH$_3$) 0.19 (3H, s, CH$_3$) 0.93 (9H, s, (CH$_3$)$_3$) 1.38–1.69 (20H, m, (CH$_2$)$_{10}$) 2.62 (1H, s, OH) 3.47–3.58 (2H, m, H-3, 5) 4.08–4.12 (1H, m, H-4) 4.15–4.27 (3H, m, H-1, 2, 6)
$[\alpha]^{26}_D = +15.13°$ (c=2.38, CHCl$_3$)
IR (CHCl$_3$): 3550 cm$^{-1}$ (—OH) 2900 cm$^{-1}$ 920 cm$^{-1}$ (Si—O—) 1440 cm$^{-1}$ 1360 cm$^{-1}$ 1200 cm$^{-1}$ 1090 cm$^{-1}$ 820 cm$^{-1}$ 740 cm$^{-1}$

(5-1) Synthesis of 1L-3-O-benzoylcarbonyl-1,2:5,6-di-O-cyclohexylidene-4-O-methoxymethyl-chiro-inositol 6 (compound C)

Compound 4 (2.60 g, 6.76 mmol) was dissolved in dichloromethane (20 ml) to which were thereafter added with cooling at 0° C. triethylamine (1.13 ml, 8.12 mmol), dimethylamino pyridine (in a catalytically effective amount) and phenylglyoxyloyl chloride (1.25 g, 7.44 mmol). The whole mixture was reacted at 0° C. for 5 minutes and at room temperature for 10 minutes, after which the reaction was terminated by addition of 1N hydrochloric acid (20 ml). The reaction mixture was subjected to extraction with ethyl acetate. After being washed with a saturated aqueous solution of sodium chloride, an ethyl acetate layer was dried over sodium sulfate anhydride and then concentrated to give a crude product. By silica gel chromatography (hexane/ethyl acetate=6/1), compound 6 was obtained as a yellowish oily product.

compound 6
yield: 3.37 g, 6.52 mmol, 97%
δ($^1$H-NMR)(CDCl$_3$): 1.26–1.84 (20H, m, (CH$_2$)$_{10}$) 0.15 (3H, s, CH$_3$) 3.36 (3H, s, OCH$_3$) 3.76 (1H, dd, J$_{5,4}$=8.2 Hz, J$_{3,4}$=11.6 Hz, H-4) 4.30–4.36 (2H, m, H-2, 5) 4.52–4.54 (2H, m, H-1, 6) 4.70, 4.92 (2H, ABq, J=6.7 Hz, CH$_2$) 5.26 (1H, dd, J$_{3,4}$=11.6 Hz, J$_{3,5}$=8.9 Hz, H-3) 7.48–7.55 (2H, m, aromatic) 7.63–7.70 (1H, m, aromatic) 8.01–8.10 (2H, m, aromatic)

(5-2) Synthesis of 1L-3-O-acetylcarbonyl-1,2:5,6-di-O-cyclohexylidene-4-O-methoxymethyl-chiro-inositol 7

The procedure of T. Mukaiyama, R. Matsueda and M. Suzuki was followed which was disclosed in Tetrahedron Lett., p. 1901 (1970).

Dissolved in dichloromethane (3 ml) were compound 4 (199 mg, 0.52 mmol), pyruvic acid (50 μl, 0.72 mmol), triphenylphosphine (190 mg, 0.724 mmol) and 2,2'-dipyridyl sulfide (160 mg, 0.724 mmol). Reaction was made with stirring at room temperature for 2 hours, whereupon 1N hydrochloric acid (3 ml) was added to bring the reaction to an end. An ethyl acetate layer, made available from extraction with ethyl acetate, was washed in turn with saturated aqueous solutions of sodium chloride, of sodium hydrogencarbonate and of sodium chloride, followed by drying over sodium sulfate anhydride and by subsequent concentration. The resultant oily product was purified by silica gel chromatography (hexane/ethyl acetate=4/1), whereby compound 7 was obtained as a yellowish oily product.

compound 7 yield: 202 mg, 0.43 mmol, 83%

$\delta$($^1$H-NMR)(CDCl$_3$): 1.26–1.69 (20H, m, (CH$_2$)$_{10}$) 2.50 (3H, s, CH$_3$) 3.32 (3H, s, OCH$_3$) 3.73 (1H, dd, $J_{5,4}$=8.2 Hz, $J_{3,4}$=11.6 Hz, H-4) 4.28 (1H, dd, $J_{5,4}$=8.2 Hz, $J_{6,5}$=5.5 Hz, H-5) 4.34 (1H, dd, $J_{3,4}$=8.6 Hz, $J_{2,5}$=5.2 Hz, H-2) 4.45–4.57 (2H, m, H-1, 6) 4.66, 4.85 (2H, ABq, J=6.4 Hz, CH$_2$) 5.05 (1H, dd, $J_{3,4}$=11.3 Hz, $J_{3,2}$=8.6 Hz, H-3)

$[\alpha]^{26}_D$=29.41° (c=0.68, CHCl$_3$)

IR (CHCl$_3$): 3000 cm$^{-1}$ (—CH) 1730 cm$^{-1}$ (ester) 1180 cm$^{-1}$ 1140 cm$^{-1}$ 1080 cm$^{-1}$ 910 cm$^{-1}$ (Si—O—) 720 cm$^{-1}$ 650 cm$^{-1}$

(5-3) Synthesis of 1L-3-O-propionylcabonyl-1,2:5,6-di-O-cyclohexylidene-4-O-methoxymethyl-chiro-inosito 1 8 (compound E)

The synthesis method of (5-2) was followed except for of compound 4 (460 mg, 1.20 mmol), triphenylphosphine (171 mg, 1.68 mmol), 2,2'-dipyridyl disulfide (369 mg, 1.68 mmol) and 2-acetoacetic acid (171 mg, 1.68 mmol). Compound 8 was obtained in oily form.

compound 8 yield: 502 mg, 1.07 mmol, 90%

$\delta$($^1$H-NMR)(CDCl$_3$): 1.13 (3H, t, J=7.3 Hz, CH$_3$CH$_2$) 1.39–1.74 (20H, m, (CH$_2$)$_{10}$) 2.85–2.95 (2H, m, CH$_3$CH$_2$) 3.32 (3H, s, OCH$_3$) 3.73 (1H, dd, $J_{5,4}$=7.9 Hz, $J_{3,4}$=11.3 Hz, H-4) 4.27 (1H, dd, $J_{5,4}$=7.9 Hz, $J_{5,6}$=5.2 Hz, H-5) 4.33 (1H, dd, $J_{3,2}$=8.6 Hz, $J_{2,1}$=5.2 Hz, H-2) 4.45–4.54 (2H, m, H-1, 6) 4.66, 4.85 (2H, ABq, J=6.7 Hz, CH$_2$) 5.06 (1H, dd, $J_{3,4}$=11.6 Hz, $J_{3,2}$=8.6 Hz, H-3)

(5-4) Synthesis of 1L-4-O-benzoylcarbonyl-3-O-t-butyldimethylsilyl-1,2:5,6-di-O-cyclohexylidene-chiroinositol 9 (compound F)

Compound 5 (735 mg, 1.62 mmol), dissolved in dichloromethane (5 ml), was incorporated at 0° C. with triethylamine (293 μl, 2.10 mmol), dimethylamino pyridine (in a catalytic amount) and then phenylglyoxyloyl chloride (297 μl, 2.43 mmol). The whole mixture was reacted with stirring at 0° C. for 5 minutes and further at room temperature for 10 minutes, followed by addition of 1N hydrochloric acid (5 ml) so as to terminate the reaction. From extraction with ethyl acetate, an ethyl acetate layer was collected and washed with a small amount of a saturated aqueous solution of sodium chloride and dried over sodium sulfate anhydride. Subsequent concentration gave a crude product which then underwent purification by silica gel chromatography (hexane/ethyl acetate=25/1). Compound 9 was thus obtained as a yellowish oily product.

compound 9 yield: 865 mg, 1.47 mmol, 91%

$\delta$($^1$H-NMR)(CDCl$_3$): 0.05 (3H, s, CH$_3$) 0.13 (3H, s, CH$_3$) 0.87 (9H, s, (CH$_3$)$_3$) 1.41–1.84 (20H, m, (CH$_2$)$_{10}$) 3.71 (1H, dd, $J_{2,3}$=7.0 Hz, $J_{3,4}$=11.1 Hz, H-b 3) 4.22 (1H, dd, $J_{2,3}$=7.0 Hz, $J_{1,2}$=6.1 Hz, H-2) 4.30 (1H, dd, $J_{4,5}$=8.6 Hz, $J_{5,6}$=6.0 Hz, H-5) 4.46 (1H, dd, $J_{1,6}$=3.4 Hz, $J_{1,2}$=6.1 Hz, H-1) 4.50 (1H, dd, $J_{1,6}$=3.4 Hz, $J_{5,6}$=6.0 Hz, H-6) 5.23 (1H, dd, $J_{3,4}$=11.1 Hz, $J_{4,5}$=8.6 Hz, H-4) 7.47–7.53 (2H, m, aromatic) 7.62–7.68 (1H, m, aromatic) 8.10–8.14 (2H, m, aromatic)

$[\alpha]^{24}_D$=−46.76° (c=2.78, CHCl$_3$)

IR (CHCl$_3$): 2900 cm$^{-1}$ 1730 cm$^{-1}$ 1680 cm$^{-1}$ 1440 cm$^{-1}$ 1340 cm$^{-1}$ 1200 cm$^{-1}$ 1080 cm$^{-1}$ 1040 cm$^{-1}$ 980 cm$^{-1}$ 920 cm$^{-1}$ 820 cm$^{-1}$ 740 cm$^{-1}$ 650 cm$^{-1}$

(5-5) Synthesis of 1L-4-O-acetylcarbonyl-3-O-t-butyldimethylsilyl-1,2:5,6-di-O-cyclohexylidene-chiro-inositol 10 (compound G)

In dichloromethane (10 ml) were dissolved compound 5 (377 mg, 0.83 mmol), pyruvic acid (144 μl, 2.07 mmol), triphenylphosphine (544 mg, 2.07 mmol) and 2,2'-dipyridyl sulfide (457 mg, 2.07 mmol). The whole mixture was reacted with stirring at room temperature for 2 hours, and 1N hydrochloric acid (15 ml) was added to terminate the reaction. By extraction of the reaction mixture with ethyl acetate, an ethyl acetate layer was collected which was then washed in turn with saturated aqueous solutions of sodium chloride, sodium hydrogencarbonate and sodium chloride, followed by drying over sodium sulfate anhydride and by subsequent concentration. The resulting oily product was silica gel-chromatographed (hexane/ethyl acetate=9/1), thereby obtaining compound 10 in yellowish oily form.

compound 10 yield: 424 mg, 0.78 mmol, 95%

$\delta$($^1$H-NMR)(CDCl$_3$): 0.01 (3H, s, Si-CH$_3$) 0.14 (3H, s, Si-CH$_3$) 0.81 (9H, s, t-Bu) 1.38–1.76 (20H, m,

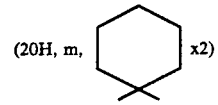

(20H, m, ⬡ x2)

2.48 (3H, s, CH$_3$) 3.69 (1H, dd, $J_{3,2}$=7.33 Hz, $J_{3,4}$=10.99 Hz, H-3) 4.17 (1H, dd, $J_{2,1}$=6.11 Hz, $J_{2,3}$=7.32 Hz, H-2) 4.31 (1H, dd, $J_{5,6}$=5.86 Hz, $J_{5,4}$=8.24 Hz, H-5) 4.39–4.47 (2H, m, H-1,6) 5.05 (1H, dd, $J_{4,5}$=8.24 Hz, $J_{4,3}$=10,99 Hz, H-4)

$[\alpha]^{26}_D$=−27.48° (c=5.35, CHCl$_3$)

IR (CHCl$_3$): 2900 cm$^{-1}$ 1720 cm$^{-1}$ 1440 cm$^{-1}$ 1350 cm$^{-1}$ 1200 cm$^{-1}$ 1080 cm$^{-1}$ 1040 cm$^{-1}$ 920 cm$^{-1}$ 830 cm$^{-1}$ 740 cm$^{-1}$

EXAMPLE 2

This example is directed to the reduction reactions of compounds 6 to 8 with use of varying reducing agents, additives and solvents. The production yields and configuration ratios of S to R are shown in Table 1. Illustrated below are details of runs 7, 14 and 15 of Table 1.

(1) Synthesis of 1L-1,2:5,6-di-O-cyclohexylidene -O-[(2S)-2-hydroxy-2-phenylacetyl]-4-methoxymethyl-chiro-inositol 61

This reaction was equivalent to run 7. A solution of compound 6 (136 mg, 0.262 mmol) in tetrahydrofuran (1 ml) was cooled at −72° C. and incorporated with a tetrahydrofuran solution of K-Selectride (0.394 ml, 0.394 mmol) as a reducing agent. Reaction was made with stirring for 10 minutes. A 5% aqueous solution of potassium hydrogensulfate was then added to terminate the reaction. The reaction mixture was extracted with ethyl acetate, after which an ethyl acetate layer was washed in turn with saturated aqueous solutions of sodium chloride, of sodium hydrogencarbonate and of sodium chloride. After being dried over sodium sulfate anhydride, the layer thus treated was vacuum-concentrated to give an oily product. Silica gel-chromatographing (hexane/ethyl acetate=4/1) led to an S-rich mixture of compound 61 of an S form and compound 62 of an R form in an S to R ratio of 97 to 3. The ratio was determined by integration of a proton signal of $OCH_2$ by means of 1H-NMR at 270 MHz.

S-rich mixture of compounds 61 and 62
yield: 108 mg, 0.207 mmol, 79%

The above mixture was recrystallized with a combined solvent of hexane and ethyl acetate (4/1, v/v), whereby compound 61 was isolated as an S-form diastereomer in a yield of 99.9%. The configuration was determinable by the rotational power of mandelic acid derivable by hydrolysis of compound 61 as will be apparent from Example 3 below.

mp : 144°–145° C.

$\delta(^1H\text{-NMR})(CDCl_3)$: 1.38–1.74 (20H, m, $(CH_2)_{10}$) 3.04 (3H, s, $OCH_3$) 3.24 (1H, dd, $J_{5,4}=7.6$ Hz, $J_{3,4}=11.3$ Hz, H-4) 3.60 (1H, d, $J=5.2$ Hz, OH) 3.65, 3.89 (2H, ABq, $J=6.7$ Hz, $CH_2$) 4.16 (1H, dd, $J_{5,6}=5.2$ Hz, $J_{4,5}=7.9$ Hz, H-5) 4.21 (1H, dd, $J_{1,2}=5.2$ Hz, $J_{2,3}=8.5$ Hz, H-2) 4.38–4.47 (2H, m, H-1, 6) 5.04 (1H, dd, $J_{3,4}=11.6$ Hz, $J_{3,2}=8.5$ Hz, H-3) 5.23 (1H, d, $J=5,2$ Hz, PhCHOH) 7.31–7.46 (5H, m, aromatic) elementary analysis:

C: 64.85, H: 7.39 (calculated)
C: 64.78, H: 7.56 (found)

(2) Synthesis of
1L-1,2:5,6-di-O-cyclohexylidene-3-O-[(2S)-2-hydroxypropanol]-4-O-methoxymethyl-chiroinositol 71

Compound 71 was produced from compound 7 as in (1) above. The configuration was adjudged by comparison of the 1H-NMR spectra to a compound derived from lactic acid.

compound 71
$\delta(^1H\text{-NMR}))(CDCl_3)$. 1.25–1.73 (20H, m, $(CH_2)_{10}$) 1.40–1.50 (3H, m, $CH_3CH(OH)$) 2.90 (1H, brs, OH) 3.36 (3H, s, $OCH_3(R)$) 3.39 (3H, s, $OCH_3(S)$) 4.65, 4.88 (2H, ABq, $J=6.4$ Hz, $CH_2(R)$) 4.69, 4.81 (2H, ABq, $J=6.4$ Hz, $CH_2(S)$) 4.90–5.09 (1H, m, H-3)

(3) Synthesis of
1L-1,2:5,6-di-O-cyclohexylidene-3-O-[(2S)-2-hydroxybutanoyl]-4-O-methoxymethyl-chiro inositol 81

Compound 81 was obtained from compound 8 as was in (1). To determine the configuration, analogy was used by comparison with compound 71. An isomeric fraction of a greater ratio was assumed to be of an S form.

compound 81
$\delta(^1H\text{-NMR})(CDCl_3)$: 1.10–1.16 (3H, m, $CH_3CH_2$) 1.20–1.30 (2H, m, $CH_3CH_2$) 1.35–1.80 (20H, m, $(CH_2)_{10}$) 2.86 (1H, brs, OH) 3.36 (3H, s, $OCH_3(R)$) 3.39 (3H, s, $OCH_3(S)$) 3.61–3.69 (1H, m, H-4) 4.20–4.30 (2H, m, H-2, 5) 4.44–4 50 (2H, m, H-1, 6) 4.64, 4.89 (2H, ABq, $J=6.4$ Hz, $CH_2(R)$) 4.68, 4.81 (2H, ABq, $J=6.4$ Hz, $CH_2(S)$) 5.03–5.11 (1H, m, H-3)

EXAMPLE 3

This example represents the reduction and hydrolysis reactions of compound 61 by which S-mandelic acid and S-1-phenyl-1,2-ethanediol are synthesized.

(1) Synthesis of S-Mandelic Acid by Hydrolysis

Compound 61 (more than 99.9% in S form) (75 mg, 0.145 mmol) was dissolved in a mixed solvent of tetrahydrofuran (0.50 ml), methanol (0.10 ml) and water (0.10 ml). To the solution cooled at 0° C. was added lithium hydroxide (12.2 mg, 0.290 mmol). The mixture was stirred at 0° C. for 3 hours, followed by addition of a saturated aqueous solution of sodium hydrogencarbonate and by washing with dichloromethane. An aqueous layer was made acidic (pH 1) with 2N hydrochloric acid and then saturated with sodium chloride. Subsequently, the layer was caused to extract with ethyl acetate. In vacuo concentration was done of an ethyl acetate layer which had been washed with a saturated aqueous solution of sodium chloride and dried over sodium sulfate anhydride, thereby giving an oily product. By bulb-to-bulb distillation there was obtained S-mandelic acid in white crystalline form.

S-mandelic acid
yield: 16.9 mg, 0.111 mmol, 77%
mp 180° C., 0.6 mmHg
$[\alpha]^{27}_D = +136°$ ($H_2O$) (found) $+158°$ ($H_2O$) (reported*) *) T. Kamanishi et al., Bull. Chem. Soc., Japan, 86, p.623 (1965)

The above product, S-mandelic acid, was treated with diazomethane to thereby give a methyl ester which was thereafter subjected to high performance liquid chromatography (HPLC). An optically active column (Chiral Cell OD, tradename, Daicel Ltd.) was used in this analysis. The product was proved to involve no racemization.

(2) Synthesis of 1-phenyl-1,2-ethanediol by reduction

A solution of compound 61 (more than 99.9% in S form) (99 mg, 0.190 mmol) in tetrahydrofuran (1.0 ml) was cooled at 0° C. and incorporated with lithium aluminum hydride ($LiAlH_4$) (10 mg, 0.27 mmol). Reaction was made with stirring at 0° C. for 30 minutes and at room temperature for 2.5 hours and thereafter terminated by addition of a saturated aqueous solution of sodium sulfate. From extraction of the reaction mixture with ethyl acetate, an ethyl acetate layer was collected, washed with a saturated aqueous solution of sodium chloride and then dried over sodium sulfate anhydride. Vacuum concentration gave a crude product. It was silica gel-chromatographed (hexane/ethyl acetate=1/1), whereby S-1-phenyl-1,2-ethanediol was obtained.

S-1-phenyl-1,2-ethanediol
yield: 15 mg, 0.108 mmol, 58%
$[\alpha]^{25}_D = +49°$ ($Et_2O$) (found) $-47.1°$ ($Et_2O$) (reported*) *) as R-isomer, "Dictionary of Organic Compounds", 5th ed., J. Buckinghum, Chapman-Hall (1982)

EXAMPLE 4

Illustrated in this example are the reduction reactions of compounds 9 and 10 in which reducers, additives and solvents are varied. The S to R ratios are listed in Table 2. Runs 2 and 8 are indicated below among the various runs of Table 2.

(1) Synthesis of 1L-3-O-t-butyldimethylsilyl-1,2:5,6-di-O-cyclohexylidene-4-O-[(2S)-2-hydroxy-2-phenylacetyl]-chiro-inositol 91

According to the procedure of run 2 of Table 2, compound 9 (56 mg, 0.095 mmol) was dissolved in tetrahydrofuran (0.5 ml). The solution after being cooled at $-72°$ C. was incorporated with a tetrahydrofuran solution of K-Selectride (95 µl, 0.095 mmol), followed by reaction with stirring for 10 minutes. A 5% aqueous solution of potassium hydrogensulfate was added to terminate the reaction. An ethyl acetate layer, generated by extraction of the reaction mixture with ethyl acetate, was washed with a staturated aqueous solution of sodium chloride and then dried over sodium sulfate anhydride. By subsequent concentration a crude product was given which was then silica gel-chromatographed (hexane/ethyl acetate=7/1) so that an S-rich mixture of compound 91 of an S form and compound 92 of an R form was obtained. The S to R ratio was 96 to 4 as determined as in the mixture of compounds 61 and 62.

S-rich mixture of compounds 91 and 92
yield: 42 mg, 0.071 mmol, 75%

$\delta(^1\text{H-NMR})(\text{CDCl}_3)$: $-0.31$ (3H, s, $CH_3$) $-0.03$ (3H, s, $CH_3$) 0.73 (9H, s, $(CH_3)_3$) 1.36–1.65 (20H, m, $(CH_2)_{10}$) 3.32 (1H, d, J=4.9 Hz, OH) 3.62 (1H, dd, $J_{2,3}$=7.0 Hz, $J_{3,4}$=11.3 Hz, H-3) 4.14 (1H, dd, $J_{2,3}$=$J_{1,2}$=6.4 Hz, H-2) 4.23 (1H, dd, $J_{4,5}$=8.6 Hz, $J_{5,6}$=5.8 Hz, H-5) 4.36–4.43 (2H, m, H-1, 6) 5.00 (1H, dd, $J_{4,5}$=8.6 Hz, $J_{3,4}$=11.0 Hz, H-4) 5.25 (1H, d, J=4.9 Hz, PhCHOH) 7.29–7.50 (5H, m, aromatic)

(2) Synthesis of 1L-3-O-t-butyldimethylsilyl-1,2:5,6-di-O-cyclohexylidene-4-O-[(2R)-2-hydroxy-2-phenylacetyl]-chiro-inositol 92

This reaction was equivalent to run 8 of Table 2. A tetrahydrofuran solution of L-Selectride (162 µl, 0.162 mmol) was added to hexamethylphosphoric triamide (35 µl, 0.20 mmol) in tetrahydrofuran (0.5 ml). Into the combined solution cooled at $-72°$ C. was incorporated compound 9 (73 mg, 0.124 mmol) previously dissolved in tetrahydrofuran (0.5 ml). Reaction was made with stirring for 10 minutes and terminated with addition of a 5% aqueous solution of potassium hydrogensulfate. Extraction was effected of the reaction mixture with ethyl acetate to thereby collect an ethyl acetate layer. It was washed with a small amount of a saturated aqueous solution of sodium chloride, dried over sodium sulfate anhydride and thereafter concentrated. Silica gel-chromatographing the resultant crude product gave an R-rich mixture of S-compound 91 and R-compound 92. The R to S ratio was 91 to 9.

R-rich mixture of compounds 91 and 92
yield: 50 mg, 0.084 mmol, 68%

$\delta(^1\text{H-NMR})(\text{CDCl}_3)$: 0.09 (3H, s, $CH_3$) 0.14 (3H, s, $CH_3$) 0.90 (9H, s, $(CH_3)_3$) 1.30–1.64 (20H, m, $(CH_2)_{10}$) 3.44 (1H, d, J=6.1 Hz, OH) 3.59 (1H, dd, $J_{2,3}$=7.0 Hz, $J_{3,4}$=11.3 Hz, H-3) 3.90 (1H, dd, $J_{4,5}$=8.4 Hz, $J_{5,6}$=6.4 Hz, H-5) 4.15 (1H, dd, $J_{2,3}$=$J_{1,2}$=7.0 Hz, H-2) 4.36 (1H, dd, $J_{1,6}$=4.0 Hz, $J_{5,6}$=6.4 Hz, H-6) 4.36 (1H, dd, $J_{1,6}$=4.0 Hz, $J_{1,2}$=7.0 Hz, H-1) 5.03 (1H, dd, $J_{3,4}$=11.3 Hz, $J_{4,5}$=8.4 Hz, H-4) 5.16 (1H, d, J=6.1 Hz, PhCHOH) 7.28–7.46 (5H, m, aromatic)

TABLE 1

| run | compound | reducing agent | equi-[5] valent | solvent | additive[6] | reaction temp (°C.) | yield (%) 61 + 62 / 71 + 72 / 81 + 82 | S:R | compound 4 (%) |
|---|---|---|---|---|---|---|---|---|---|
| 1 | 6 | NaBH$_4$ | 1.0 | ethanol | — | 0 | 44 | 60:40 | 6 |
| 2 | 6 | iso-Bu$_2$AlH | 1.0 | toluene | — | −72 | 46 | 52:48 | 8 |
| 3 | 6 | reduced aluminum[1] | 1.0 | " | — | −72~0 | 15 | 33:67 | 49 |
| 4 | 6 | LiBH$_4$ | 1.0 | tetrahydrofuran | — | −72 | 83 | 52:48 | 0 |
| 5 | 6 | LiEt$_3$BH | 1.0 | " | — | −72 | 93 | 44:56 | 0 |
| 6 | 6 | K-Selectride[2] | 1.2 | " | — | −72 | 85 | 86:14 | 0 |
| 7 | 6 | " | 1.5 | diethyl ether | — | −72 | 79 | 97:3 | 0 |
| 8 | 6 | " | 1.7 | " | — | −72 | 83 | 96:4 | 0 |
| 9 | 6 | " | 1.7 | tetrahydrofuran | 18-crown-6 | −72 | 78 | 10:90 | 0 |
| 10 | 6 | " | 1.7 | diethyl ether | " | −72 | 65 | 23:77 | 0 |
| 11 | 6 | L-Selectride[3] | 1.4 | " | — | −72 | 86 | 76:24 | 0 |
| 12 | 6 | " | 1.4 | " | HMPA[4] | −72 | 78 | 12:88 | 0 |
| 13 | 6 | " | 1.3 | tetrahydrofuran | " | −72 | 79 | 10:90 | 0 |
| 14 | 7 | " | 1.0 | " | — | −72 | 62 | 88:12 | 0 |
| 15 | 8 | " | 1.0 | diethyl ether | — | −72 | 90 | 80:20 | 7 |

[1] Na[AlH$_2$(OCH$_2$CH$_2$OCH$_3$)$_2$], Red-Al, Aldrich Co.
[2] KB[CH(CH$_3$)C$_2$H$_5$]$_3$H
[3] LiB[CH(CH$_3$)C$_2$H$_5$]$_3$H
[4] [(CH$_3$)$_2$N]$_3$PO
[5] mol of reducing agent per one mol of compound to be reduced
[6] use of 1.3 times by mol ratio of compound to be reduced

TABLE 2

| run[7] | compound | reducing agent | equi-[5] valent | solvent | additive[6] | yield (%) 91 + 92 / 101 + 102 | S:R |
|---|---|---|---|---|---|---|---|
| 1 | 9 | K-Selectride[2] | 1.0 | diethyl ether | — | 56 | 96:4 |
| 2 | 9 | " | 1.0 | tetrahydrofuran | — | 75 | 96:4 |
| 3 | 9 | " | 1.2 | " | HMPA[4] | 72 | 54:46 |
| 4 | 9 | " | 1.2 | " | 18-crown-6 | 66 | 4:96 |
| 5 | 9 | L-Selectride[3] | 1.3 | diethyl ether | — | 63 | 96:4 |
| 6 | 9 | " | 1.3 | tetrahydrofuran | — | 77 | 59:41 |
| 7 | 9 | " | 1.3 | " | 12-crown-4 | 71 | 29:71 |
| 8 | 9 | " | 1.3 | " | HMPA | 68 | 9:91 |
| 9 | 9 | " | 1.3 | " | TMEDA[1] | 54 | 63:37 |

TABLE 2-continued

| run*[7] | compound | reducing agent | equi-*[5] valent | solvent | additive*[6] | yield (%) 91 + 92 101 + 102 | S:R |
|---|---|---|---|---|---|---|---|
| 10 | 9 | LiEt$_3$BH | 1.0 | diethyl ether | — | 71 | 96:4 |
| 11 | 10 | L-Selectride | 1.3 | " | — | 84 | 91:9 |
| 12 | 10 | " | 1.3 | " | HMPA | 68 | 27:73 |
| 13 | 10 | " | 1.3 | tetrahydrofuran | — | 82 | 69:31 |
| 14 | 10 | " | 1.3 | " | HMPA | 76 | 29:71 |
| 15 | 10 | " | 1.0 | " | — | 61 | 98:2 |
| 16 | 10 | " | 1.2 | " | 18-crown-6 | 61 | 34:66 |
| 17 | 10 | " | 1.3 | " | HMPA | 67 | 90:10 |

*[1]$(CH_3)_2NCH_2CH_2N(CH_3)_2$
*[2] to *[5] same as footnotes to Table 1
*[6]use of 1.6 times by mol ratio of compound 9 to be reduced and of 1.3 times by mol ratio of compound 10 to be reduced
*[7]all runs at −72° C. reaction temperature

What is claimed is:

1. The compound of 1L-1,2:5,6-di-O-cyclohexylidene-3-O-methoxymethyl-chiro-inositol.

2. The compound of 1L-3-O-t-butyldimethylsilyl-1,2:5,6-di-O-cyclohexylidene-chiro-inositol.

3. The compound of 1L-3-O-benzoylcarbonyl-1,2:5,6-di-O-cyclohexylidene-4-O-methoxymethyl-chiro-inositol.

4. The compound of 1L-3-O-acetylcarbonyl-1,2:5,6-di-O-cyclohexylidene-4-O-methoxymethyl-chiro-inositol.

5. The compound of 1L-3-O-propionylcarbonyl-1,2:5,6-di-O-cyclohexylidne-4-O-methoxymethyl-chiro-inositol.

6. The compound of 1L-4-O-benzoylcarbonyl-3-O-t-butyldimethylsilyl-1,2:5,6-di-O-cyclohexylidene-chiroinositol.

7. The compound of 1L-4-O-acetylcarbonyl-3-O-t-butyldimethylsilyl-1,2:5,6-di-O-cyclohexylidene-chiroinositol.

* * * * *